United States Patent
Yang et al.

(10) Patent No.: US 6,306,284 B1
(45) Date of Patent: Oct. 23, 2001

(54) APPARATUS AND METHOD FOR MONITORING FLUORINE IONS

(75) Inventors: Feng-Yi Yang, Taipei; Wei-tien Huang, Hsin-Chu, both of (TW)

(73) Assignee: Taiwan Semiconductor Manufacturing Company, Ltd., Hsin Chu (TW)

( * ) Notice: Subject to any disclaimer, the term of this patent is extended or adjusted under 35 U.S.C. 154(b) by 0 days.

(21) Appl. No.: 09/243,775

(22) Filed: Feb. 3, 1999

(51) Int. Cl.[7] .................................................. G02N 27/26
(52) U.S. Cl. .............................. 205/778.5; 205/787.5; 205/433; 205/789; 204/416
(58) Field of Search .............................. 204/400, 416, 204/433; 205/775, 778.5, 789, 787.5

(56) References Cited

U.S. PATENT DOCUMENTS 3,431,182 * 3/1969 Frant .................................. 205/778.5
4,131,428 * 12/1978 Diggens ........................... 205/778.5
4,263,104 * 4/1981 Diggens et al. ................... 205/778.5

FOREIGN PATENT DOCUMENTS

358058189A * 11/1991 (JP) .
403250309 A * 11/1991 (JP) .

OTHER PUBLICATIONS

JPAB abstract of Iizuka (JP 403250309 A), Nov. 1991.*
JPAB abstract of Sakai (JP 358058189A), Apr. 1983.*

* cited by examiner

Primary Examiner—T. Tung
Assistant Examiner—Alex Noguerola
(74) Attorney, Agent, or Firm—Tung & Associates

(57) ABSTRACT

An apparatus and a method for determining concentration of fluorine ions in aqueous solutions are provided. In the apparatus, a pH sensor is provided for sensing a pH value of an aqueous solution to be determined. A pH controller is then used to compare the pH value determined with stored pH data to determine whether the aqueous solution is acidic or alkalinic. An acid dispenser or a base dispenser is then used to dispense either an acid or a base into the pH adjustment tank for adjusting the pH value of the aqueous solution to within a desirable range. For instance, for the detection of fluorine ions, a suitable pH range is between about 4 and about 10. After the pH value is stabilized in the aqueous solution, a fluorine ion sensor may be used to sense the fluorine ion concentration in the aqueous solution. A common acid and base which may be used to bring the pH value within the desirable range may be $H_2SO_4$ and NaOH.

16 Claims, 3 Drawing Sheets

APPARATUS AND METHOD FOR MONITORING FLUORINE IONS

FIELD OF THE INVENTION

The present invention generally relates to an apparatus and a method for monitoring fluorine ions in an aqueous solution and more particularly, relates to an apparatus and a method for determining fluorine ion concentration in an aqueous solution wherein the pH value of the aqueous solution is first stabilized within a range between about 4 and about 10 in which the fluorine ion concentration is independent of the pH value of the aqueous solution.

BACKGROUND OF THE INVENTION

Various industrial fabrication processes often employ apparatus for dispensing pre-selected, discrete amounts or doses of a fluid medium for anyone of many different purposes. For example, in connection with semiconductor fabrication operations for producing semiconductor devices from silicon wafers, various processing equipment produces waste water of which the pH value must be controlled. This is usually accomplished by measuring the pH of the waste water and then adding doses of a buffer solution to the waste water from time to time such that the pH value of the waste water is maintained within a pre-selected, allowed range.

For instance, waste water which is produced by an ion implantation equipment usually contains a concentration of fluorine ions. Based on the regulations of environmental protection agency, such concentration can not be higher than 15 ppm when the waste water is released into the environment. It is therefore important that the concentration of fluorine ions in the waste water must be determined accurately. When determining the fluorine ion concentration, it was found that the fluorine ion concentration varies with the pH values of the waste water except in a relatively narrow range. For instance, FIG. 1 shows the electrical potentials for aqueous solutions that contain different concentrations of fluorine ions plotted against the pH values of the aqueous solutions. As shown in FIG. 1, three different fluorine ion concentrations, i.e., 2 mg/l, 5 mg/l and 10 mg/l plotted. For all three concentrations, the electrical potential is not constant at various pH levels except within a relatively narrow range of between about 4 and about 10.

The measurement of fluorine ion concentrations in waste water therefore presents a challenge in that the pH value of the waste water must first be adjusted to within the range of pH where the electrical potentials are constant so that the fluorine ion concentration can be reliably determined.

Conventionally, a buffer solution which is substantially of alkaline nature is added to the aqueous solution to stabilize the chemistry prior to a pH determination. For instance, a 1% alkaline solution of $CH_3COONa$ has been utilized as the buffer solution. The buffer solution is normally added to the waste water at a constant rate regardless whether it is necessary or whether the waste water is of an acidic nature. The conventional apparatus for dispensing such buffer solutions is therefore inadequate in providing a stabilized aqueous solution for the detection of fluorine ion concentrations. This is particularly the case when a waste water is already alkaline and the addition of the buffer solution further increases its alkalinity.

It is therefore an object of the present invention to provide an apparatus for determining concentration of fluorine ions in an aqueous solution that does not have the drawbacks or shortcomings of the conventional apparatus.

It is another object of the present invention to provide an apparatus for determining concentration of fluorine ions in an aqueous solution that is capable of producing accurate results.

It is a further object of the present invention to provide an apparatus for determining concentration of fluorine ions in an aqueous solution that is capable of making pH adjustment in the solution prior to the determination of the fluorine ion concentration.

It is another further object of the present invention to provide an apparatus for determining concentration of fluorine ions in an aqueous solution which includes a pH controller, an acid dispenser, a base dispenser and a fluorine ion sensor.

It is still another object of the present invention to provide an apparatus for determining concentration of fluorine ions in an aqueous solution which is capable of adjusting automatically a pH value of the solution to within a 4~10 range before determining the concentration of fluorine ions.

It is yet another object of the present invention to provide an apparatus for determining concentration of fluorine ions in an aqueous solution which incorporates an acid dispenser that dispenses $H_2SO_4$ and a base dispenser which dispenses NaOH.

It is still another further object of the present invention to provide a method for determining concentration of fluorine ions in an aqueous solution by first adding $H_2SO_4$ or NaOH to the solution such that the pH value of the solution falls within the range of 4~10.

It is yet another further object of the present invention to provide a method for determining concentration of fluorine ions in an aqueous solution by adding a buffer solution, an acid or a base into the aqueous solution until a pH value between 4 and 10 is obtained.

SUMMARY OF THE INVENTION

In accordance with the present invention, an apparatus and a method for determining concentration of fluorine ions in an aqueous solution are provided.

In a preferred embodiment, an apparatus for determining concentration of fluorine ions in aqueous solutions is provided which includes a pH adjustment tank for holding an aqueous solution, a pH sensor for sensing a pH value of the aqueous solution in the tank and sending a first signal to a pH controller, a pH controller for receiving the first signal, comparing to a stored pH value, sending out a second signal when the first signal is larger than the stored pH value or sending out a third signal when the first signal is smaller than the stored pH value, an acid dispenser which receives the second signal and delivers an acid to the aqueous solution in the tank, a base dispenser which receives the third signal and delivers a base to the aqueous solution in the tank, and a fluorine ion sensor for sensing a fluorine ion concentration in the aqueous solution which has a modified pH value in the pH adjustment tank.

The apparatus for determining concentration of fluorine ions in aqueous solutions may further include a buffer solution dispenser for delivering a buffer solution to the aqueous solution in the pH adjustment tank. The stored pH value in the pH controller may be in a range between about 4 and about 10. The aqueous solution may be a waste water flow from a semiconductor fabrication facility. A second signal is sent by the pH controller to the acid dispenser to when the first signal is indicative of a pH value larger than about 10. A third signal is sent by the pH controller to the base dispenser when the first signal is indicative of a pH value smaller than about 4. The acid dispenser delivers $H_2SO_4$ to the aqueous solution in the tank. The base dispenser delivers NaOH to the aqueous solution in the tank. The modified pH value in the tank is in the range between about 4 and about 10. The apparatus may further include a recording device for recording the fluorine ion concentration detected by the fluorine ion sensor.

The present invention is further directed to a method for determining concentration of fluorine ions in aqueous solutions which can be carried out by the operating steps of first filling a pH adjustment tank with an aqueous solution, sensing a pH value of the aqueous solution in the tank by a pH sensor and sending a first signal to a pH controller, receiving a first signal in the pH controller for comparing to a stored pH value, sending a second signal from the pH controller to an acid dispenser when the first signal is larger than the stored pH value for delivering an acid to the aqueous solution, sending a third signal from the pH controller to a base dispenser when the first signal is smaller than the stored pH value for delivering a base to the aqueous solution, and detecting a fluorine ion concentration in the aqueous solution which has a modified pH value in the tank by a fluorine ion sensor.

The method for determining concentration of fluorine ions in aqueous solutions may further include the step of delivering a buffer solution to the aqueous solution in the pH adjustment tank. The buffer solution may be a 1% solution of $CH_3COONa$. The method may further include the step of storing a range of pH values from about 4 to about 10 in the pH controller. The method may further include the step of filling a pH adjustment tank with waste water from a semiconductor fabrication facility.

The method for determining concentration of fluorine ions in aqueous solutions may further include the step of sending the second signal from the pH controller to the acid dispenser when the first signal is indicative of a pH value of larger than about 10. The method may further include the step of sending the third signal from the pH controller to the base dispenser when the first signal is indicative of a pH value of smaller than about 4. The method may further include the step of delivering $H_2SO_4$ from the acid dispenser to the aqueous solution in the tank, or include the step of delivering NaOH from the base dispenser to the aqueous solution in the tank. The method may further include the step of modifying a pH value in the tank to within a range between about 4 and about 10.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

The present invention discloses an apparatus for determining concentration of fluorine ions in an aqueous solution which is equipped with a pH controller that works in conjunction with an acid dispenser and a base dispenser such that the pH value of the aqueous solution can be suitably adjusted prior to the determination of the fluorine ion concentration. In the apparatus, a pH adjustment tank is used to hold an aqueous solution. The tank is equipped with a pH sensor for sensing a pH value of the solution in the tank and then sending a first signal to a pH controller that is capable of comparing the first signal to a pre-stored pH value. When the first signal is larger than the stored pH value, a second signal is sent out to an acid dispenser for delivering an acid to the aqueous solution in the tank. When the first signal is smaller than the stored pH value, a third signal is sent out to a base dispenser for delivering a base to the aqueous solution in the tank. After the pH value of the aqueous solution is adjusted, a fluorine ion sensor is used for sensing the fluorine ion concentration in the aqueous solution.

It has been found that within a pH value between about 4 and about 10, the electrical potential of an aqueous solution that contains various fluorine ion concentrations is stable in a pH range between about 4 and about 10. The present invention apparatus is therefore capable of automatically adjusting the pH value of an aqueous solution by adding either an acid or a base prior to the determination of the fluorine ion concentration. The present invention apparatus may further utilize a buffer solution dispenser which dispenses a buffer solution into the aqueous solution simultaneously with the addition of an acid or a base such that possible interferences with other ions which may be contained in the solution can be minimized. The buffer solution may be fed to the pH adjustment tank by a positive displacement piston pump.

The present invention further discloses a method for determining concentration of fluorine ions in aqueous solutions by first determining a pH value of the aqueous solution in the tank by a pH sensor and then comparing the value with a pre-stored pH range. When the value determined is higher than the stored pH range, i.e., when the solution is of an alkaline nature, an acid is dispensed to the aqueous solution by opening a value and feeding the acid from an acid storage tank. When the pH value measured is smaller than the pre-stored pH range, a base solution is fed into the aqueous solution by opening a value and feeding the base solution from a base solution storage tank. After the pH value of the aqueous solution is adjusted, the fluorine ion concentration can be determined by a fluorine ion sensor.

Figure 2:
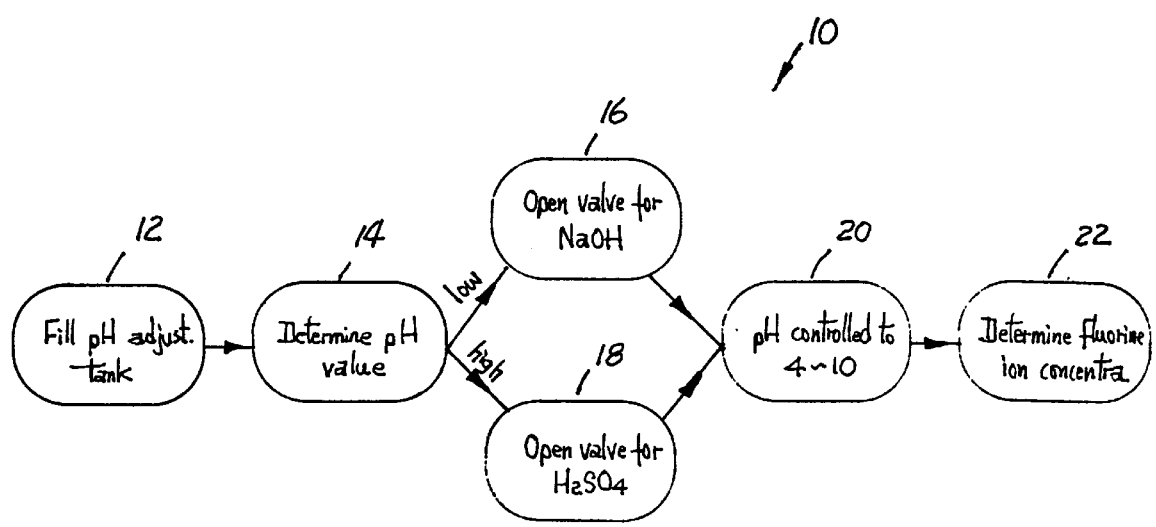
FIG. 2 is a process flow chart for the present invention method.

Referring now to FIG. 2, wherein a process flow chart 10 for the present invention novel method is shown. In the process flow chart 10, step 12 is first carried out by filling a pH adjustment tank with an aqueous solution in which the fluorine ion concentration is to be determined. In the next step 14, a pH sensor is used to determine the pH value of the aqueous solution that was filled into the pH adjustment tank. When the pH value determined is to low, i.e., below 4 which indicates an acidic nature of the aqueous solution, step 16 is executed which opens a valve for a flow of a base solution such as NaOH. On the other hand, when the pH value determined in step 14 is higher than that stored, i.e., higher than 10, which indicates an alkaline nature of the aqueous solution, a valve is opened for feeding a flow of an acid such as $H_2SO_4$ into the aqueous solution. This is shown in step 18. After the pH value of the aqueous solution is adjusted to a suitable range, i.e., between about 4 and about 10, as shown in step 20, a fluorine ion sensor is used to determine the fluorine ion concentration in the aqueous solution as shown in step 22.

Figure 3:
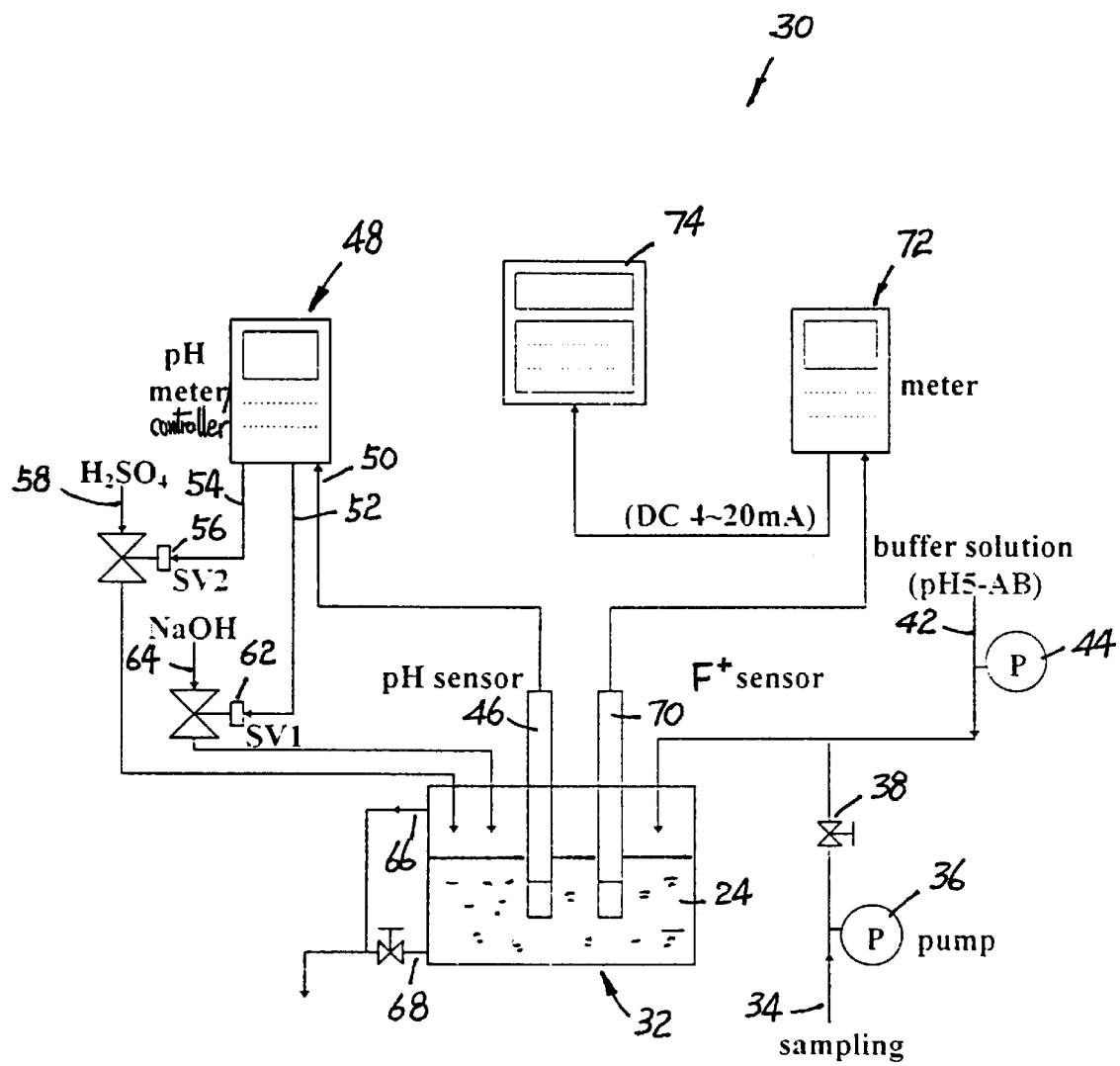
FIG. 3 is a schematic illustrating the present invention apparatus for automatically adjusting the pH value of an aqueous solution to within a range of 4~10.

A detailed construction of the present invention novel apparatus 30 is shown in FIG. 3. In the apparatus 30, a pH adjustment tank 32 is first provided. Into the pH adjustment tank 32, a waste water sample 34 is fed by pump 36 through shut-off valve 38. Simultaneously with the feeding of the waste water sample 34, a commercially available buffer solution 42 such as a 1% solution of $CH_3COONa$ in water can be fed into the pH adjustment tank 32 by pump 44. The buffer solution used normally has a pH value of about 5 for stabilizing the aqueous solution to be detected. The dosing pump 44 delivers the buffer solution into the aqueous solution to further reduce any possible interference by other types of ions existing in the aqueous solution.

Figure 1:
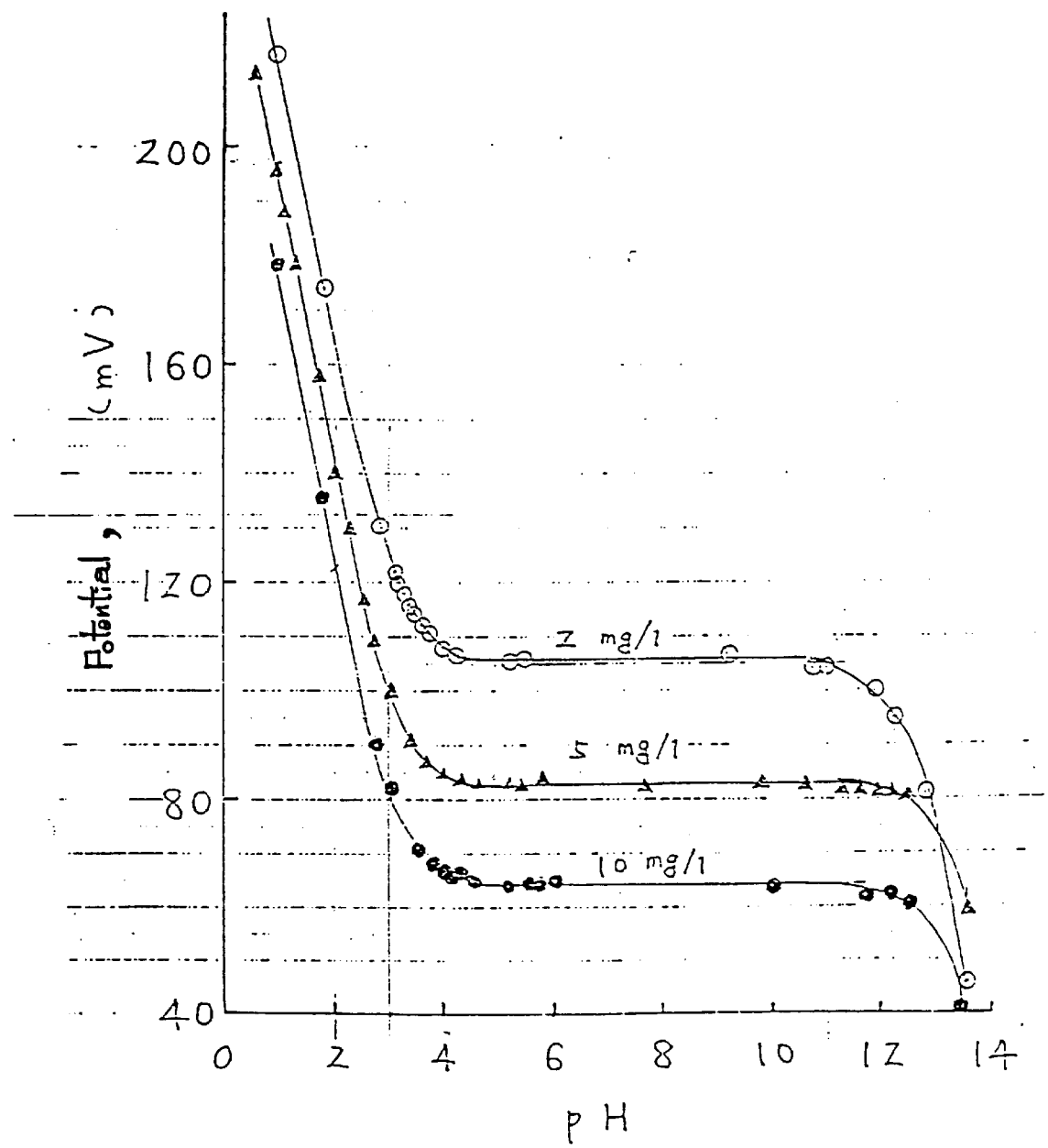
FIG. 1 is a graph illustrating electrical potentials plotted against pH values for three aqueous solutions containing different concentrations of fluorine ions.

Into the pH adjustment tank 32, a pH sensor 46 is positioned to first determine the pH value of the aqueous solution 24. The pH value of the aqueous solution 24 can be read in a pH meter 48 which is also a pH controller. In the pH controller 48, a range of pH values is first stored such that it can be used to compare with the pH reading detected by sensor 46. For fluorine ions, as shown in FIG. 1, it is desirable to measure the concentration of fluorine ions in an area where the electrical potentials of the aqueous solution is independent of the pH values. Once the pH value measured by sensor 46 is compared to the pH range, i.e., between about 4 and about 10, either a second signal 52 or a third signal 54 may be sent out to a shut-off valve for a base tank and an acid tank, respectively. When the measurement of the first signal 50 is larger than 10 in pH, a third signal 54 is sent out to a shut-off valve 56 and thus opens the valve to feed a flow of acid 58 such as $H_2SO_4$ into the pH adjustment tank 32 such that acid is mixed with the aqueous solution 24. A mixing means (not shown) is frequently provided in the pH adjustment tank 32.

When the first signal 50 of the pH value in the aqueous solution 24 is measured to be smaller than 4, i.e., when the aqueous solution is highly acidic, a second signal 52 is sent to a shut-off valve 62 such that a flow of base 64 such as NaOH can be sent to the pH adjustment tank 32. With the addition of the acid or the base into the aqueous solution 24, the pH value of the aqueous solution 24 can be suitably adjusted within the range of 4~10. The pH adjustment tank is further provided with an overflow valve 66 and a drain valve 68 to prevent the tank 32 from over flowing and to drain the tank, respectively.

In the next step of the process, as shown by the apparatus in FIG. 3, a fluorine ion sensor 70 is utilized to determine the fluorine ion content in the aqueous solution 24 and to send a signal to a fluorine ion meter 72 for displaying a reading. The fluorine ion concentration read from the aqueous solution 24 may further be recorded in a data recorder 74 for the fluorine ion concentration. It has been found that in the normal operation of detecting a waste water flow from an ion implantation apparatus, the waste water has a pH value of between about 2 and 3, i.e, the waste water is acidic and therefore a base such as NaOH is added to bring up the pH value to within the range of 4~10.

The present invention novel apparatus and method have therefore been amply demonstrated in the above descriptions and in the appended drawings of FIGS. 2 and 3. It should be noted that while an acid of $H_2SO_4$ and a base of NaOH have been illustrated in the preferred embodiment of the invention, any other acid or base can be utilized to provide the same desirable result of the present invention apparatus and method. Furthermore, while the present invention is illustrated for fluorine ions, the same apparatus and method may be utilized in the detection of other types of ions that are frequently encountered in semiconductor fabrication processes as long as a stable range of pH values must first be obtained in order to make accurate determination of the ion concentration.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows:

1. An apparatus for determining concentration of fluorine ions in aqueous solutions comprising:
    a pH adjustment tank holding an aqueous solution therein,
    a pH sensor for sensing a pH value of said aqueous solution in said tank and sending a first signal to a pH controller,
    a pH controller for receiving said first signal, comparing to a stored pH value, sending out a second signal when said first signal is larger than a pH value of 10 or sending out a third signal when said first signal is smaller than a pH value of 4,
    an acid dispenser for receiving said second signal and delivering an acid to said aqueous solution in said tank,
    a base dispenser for receiving said third signal and delivering a base to said aqueous solution in said tank, and
    a fluorine ion sensor for sensing a fluorine ion concentration in said aqueous solution having a modified pH value in said pH adjustment tank.

2. An apparatus for determining concentration of fluorine ions in aqueous solutions according to claim 1 further comprising a buffer solution dispenser for delivering a buffer solution to said aqueous solution in said pH adjustment tank.

3. An apparatus for determining concentration of fluorine ions in aqueous solutions according to claim 1, wherein said stored pH value is a range between about 4 and about 10.

4. An apparatus for determining concentration of fluorine ions in aqueous solutions according to claim 1, wherein said aqueous solution is waste water from a semiconductor fabrication facility.

5. An apparatus for determining concentration of fluorine ions in aqueous solutions according to claim 1, wherein said acid dispenser delivers $H_2SO_4$ to said aqueous solution in said tank.

6. An apparatus for determining concentration of fluorine ions in aqueous solutions according to claim 1, wherein said base dispenser delivers NaOH to said aqueous solution in said tank.

7. An apparatus for determining concentration of fluorine ions in aqueous solutions according to claim 1, wherein said modified pH value in said tank is in the range between about 4 and about 10.

8. An apparatus for determining concentration of fluorine ions in aqueous solutions according to claim 1 further comprising a recording device for recording the fluorine ion concentration detected by said fluorine ion sensor.

9. A method for determining concentration of fluorine ions in aqueous solutions comprising the steps of:
    filling a pH adjustment tank with an aqueous solution,
    sensing a pH value of said aqueous solution in said tank by a pH sensor and sending a first signal to a pH controller,
    receiving said first signal in said pH controller for comparing to a stored pH value,
    sending a second signal from said pH controller to an acid dispenser when said first signal is larger than a pH value of 10 for delivering an acid to said aqueous solution, sending a third signal from said pH controller to a base dispenser when said first signal is smaller than a pH value of 4 for delivering a base to said aqueous solution, and detecting a fluorine ion concentration in said aqueous solution by a fluorine ion sensor, said aqueous solution in said tank having a modified pH value.

10. A method for determining concentration of fluorine ions in aqueous solutions according to claim 9 further comprising the step of delivering a buffer solution to said aqueous solution in said pH adjustment tank.

11. A method for determining concentration of fluorine ions in aqueous solutions according to claim 9 wherein said buffer solution is a 1% solution of $CH_3COONa$.

12. A method for determining concentration of fluorine ions in aqueous solutions according to claim 9 further comprising the step of storing a range of pH values from about 4 to about 10 in said pH controller.

13. A method for determining concentration of fluorine ions in aqueous solutions according to claim 9 further comprising the step of filling a pH adjustment tank with waste water from a semiconductor fabrication facility.

14. A method for determining concentration of fluorine ions in aqueous solutions according to claim 9 further comprising the step of delivering $H_2SO_4$ from said acid dispenser to said aqueous solution in said tank.

15. A method for determining concentration of fluorine ions in aqueous solutions according to claim 9 further comprising the step of delivering NaOH from said base dispenser to said aqueous solution in said tank.

16. A method for determining concentration of fluorine ions in aqueous solutions according to claim 9 further comprising the step of modifying a pH value in said tank to within a range between about 4 and about 10.

* * * * *